(12) United States Patent
Wakita et al.

(10) Patent No.: US 7,253,886 B2
(45) Date of Patent: Aug. 7, 2007

(54) ANALYSIS DEVICE AND ANALYSIS DISC USED FOR THE SAME

(75) Inventors: Tsugio Wakita, Matsuyama (JP); Hiroyuki Hamamoto, Imabari (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 172 days.

(21) Appl. No.: 10/515,269

(22) PCT Filed: May 23, 2003

(86) PCT No.: PCT/JP03/06501

§ 371 (c)(1),
(2), (4) Date: Nov. 22, 2004

(87) PCT Pub. No.: WO03/102556

PCT Pub. Date: Dec. 11, 2003

(65) Prior Publication Data

US 2006/0039002 A1    Feb. 23, 2006

(30) Foreign Application Priority Data

May 30, 2002   (JP)   .............................. 2002-156532

(51) Int. Cl.
*G01N 21/00* (2006.01)
(52) U.S. Cl. ...................................................... 356/73
(58) Field of Classification Search .................. 356/73; 250/201.1–201.5, 201
See application file for complete search history.

(56) References Cited

U.S. PATENT DOCUMENTS 5,121,371 A * 6/1992 Farnsworth et al. ..... 369/44.26
6,185,178 B1 * 2/2001 Noh ........................... 369/126
6,803,999 B1 * 10/2004 Gordon ........................ 356/73
7,033,747 B2 * 4/2006 Gordon ........................ 435/4
7,061,594 B2 * 6/2006 Worthington et al. ......... 356/72
2002/0118355 A1 * 8/2002 Worthington et al. ......... 356/72
2002/0151043 A1 * 10/2002 Gordon ................... 435/287.2
2002/0171838 A1 * 11/2002 Pal et al. .................... 356/436

FOREIGN PATENT DOCUMENTS

| JP | 9-237914       | 9/1997 |
| JP | 2000-173080    | 6/2000 |
| JP | 2001-4519      | 1/2001 |
| WO | WO 01/53831 A1 | 7/2001 |

\* cited by examiner

*Primary Examiner*—Layla G. Lauchman
*Assistant Examiner*—J. Underwood
(74) *Attorney, Agent, or Firm*—Steptoe & Johnson LLP

(57) ABSTRACT

It is an object of the present invention to provide an analysis device which can reproduce an image of an analysis object more accurately even when an analysis disc is an optical disc having the analysis object therein. A second pickup (106b) is provided for capturing and tracing a track on an analysis disc (201), and a first pickup (106a) is provided which is fixed at a constant distance (L) from the second pickup (106b) on the disc. A signal identical to the tracking signal of the second pickup (106b) is applied to a tracking actuator for driving the optical path of the first pickup (106a) in the radial direction of the analysis disc. A part of an analysis object (110) is traced and read while the position of the second pickup (106b) in the radial direction is controlled at times.

6 Claims, 8 Drawing Sheets

(a)

(b)

(a)

(b)

ANALYSIS DEVICE AND ANALYSIS DISC USED FOR THE SAME

TECHNICAL FIELD

The present invention relates to an analysis device in which an analysis object such as blood is set in an optical disc for analysis and the analysis object is traced and captured as an image.

BACKGROUND ART

As disclosed in National Publication of International Patent Application No. 10-504397 and others, methods are available in which an analysis object to be tested is disposed in a certain portion on a disc and the analysis object is traced to obtain an image of the analysis object by using the reproducing function of the optical disc.

As shown in FIGS. 7 and 8, an optical disc 101 generally has tracks 102 of an aluminum reflective layer that are formed on a surface of a base 101b. Information is recorded on pits and grooves 103 which are asperities finely formed on the tracks. Reference numeral 104 denotes a protective layer.

In a typical optical disc drive shown in FIG. 6, reading is performed on the tracks 102 by a laser beam Ph from a pickup 106 while the optical disc 101 is rotated in the direction of arrow C by a disc motor 105. The pickup 106 is screwed onto a feed screw 109 driven by a traverse motor 108. A servo control circuit 107 drives the traverse motor 108 to move the pickup 106 in the radial direction in such a way that the tracks 102 are traced according to the reproduction output of the pickup 106. Further, the servo control circuit 107 detects address information recorded on the tracks 102 and drives (CLV control) the disc motor 105 with a constant linear velocity.

To be specific, regarding the irradiation position of the laser beam Ph on the optical disc 101, the optical path of the laser beam Ph is driven not only by driving the traverse motor 108 but also a tracking actuator (not shown), which is provided in the pickup 106, in the lateral direction (radial direction) with respect to a surface of the optical disc 101 as necessary, and the tracks 102 are accurately traced while tracking control is performed.

In the case of an analysis disc unlike audio CDs and video CDs, an analysis object 110 is further disposed in the optical disc 101 as shown in FIGS. 7 and 8. In an analysis device using the technique of a conventional optical disc drive, the analysis object 110 is read by the pickup 106 and is processed by a video signal processing circuit 111 to obtain an image of the analysis object 110.

When using the address information of a coded signal written on the track on the disc, the address information may not be captured well due to a servo disturbance of focusing and tracking during the passage of the analysis object 110.

On a part where the analysis object 110 is present, the pits and grooves cannot be disposed. Even if the pits and grooves are present, it is quite difficult to read signals on the pits and grooves because of the influence of the analysis object 110. Such a part corresponds to a defect on an optical disc and thus a rotary servo, a tracking servo, and a focus servo on the optical disc do not normally operate when passing through the part. As a result, a number of problems frequently occur. For example, the rotation of the disc is disturbed during the passage through the part corresponding to the analysis object 110, and an adjacent track is caught after the passage of the part corresponding to the analysis object 110. Some measures are available to keep each servo in a holding state only on a defect. However, the holding state cannot be positively kept because each servo is out of control. As the number of disposed analysis objects increases, the number of unstable regions increases, resulting in greater influence of the servo disturbance. Further, similar problems occur in the rotary servo control of a disc.

DISCLOSURE OF THE INVENTION

It is an object of the present invention to provide an analysis device which can reproduce an image of an analysis object more accurately even when an analysis disc is an optical disc having the analysis object therein.

In an analysis device of the present invention for irradiating an analysis disc having an analysis object therein with detection light and for reading a state of the analysis object, the analysis device is capable of setting therein the analysis disc where a first reading area having the analysis object and a second reading area not having the analysis object are recorded with different diameters, and the analysis device comprises a first pickup for irradiating the first reading area of the set analysis disc with detection light and detecting detection light from the first reading area, and a second pickup for irradiating the second reading area of the set analysis disc with detection light and detecting track information from the detection light of the second reading area. Traverse control is performed to keep a constant interval in the radial direction of the analysis disc between the first pickup and the second pickup, thereby to integrally move the first and second pickups in the radial direction. A tracking signal is supplied to the tracking actuator of the second pickup so as to drive the optical path of the second pickup in the radial direction of the analysis disc and trace tracks, and a signal identical to the tracking signal of the second pickup is applied to the tracking actuator of the first pickup for driving the optical path of the first pickup in the radial direction of the analysis disc, so as to read the analysis object.

Further, the first pickup has the function of reading an image on a reading position of the analysis disc but does not have the function of reading the track information.

Moreover, both of the two pickups have the function of reading an image on a reading position of the analysis disc and the function of reading the track information. Automatic switching is performed so that one of the pickups is caused to act as the second pickup, the pickup having read the track information from the analysis disc, and the other pickup is caused to act as the first pickup.

Besides, a plurality of first pickups are provided for reading the first reading area.

An analysis disc of the present invention in which a first reading area and a second reading area are formed in different diameter ranges, respectively is such that a coded signal traceable by a pickup is optically recorded but an analysis object is not disposed in the second reading area, and the analysis object is disposed but the coded signal traceable by the pickup is not optically recorded in the first reading area.

An optical disc of the present invention, in which a first reading area and a second reading area are formed with different diameters, wherein a coded signal traceable by a pickup is optically recorded in the first and second reading areas, and an analysis object is disposed only in the first reading area of the first and second reading areas.

Further, according to the analysis disc of the present invention, the second reading area is larger than or equal to the first reading area in width.

Moreover, according to the analysis device of the present invention, a focus voltage required for causing the second pickup to just focus on a track is set as a reference voltage, the second pickup detecting detection light from the second reading area not having the analysis object, so that a voltage obtained by adding an offset voltage to the reference voltage is applied to the focus actuator of the first pickup for detecting detection light from the first reading area having the analysis object disposed therein, thereby to trace the analysis object to obtain its image, and the offset voltage is varied to change the focus position of the first pickup, thereby to repeatedly trace the analysis object to obtain its image in a three-dimensional manner.

BEST MODE FOR CARRYING OUT THE INVENTION

Referring to FIGS. 1 to 5, embodiments of the present invention will be described below.

Figure 6:
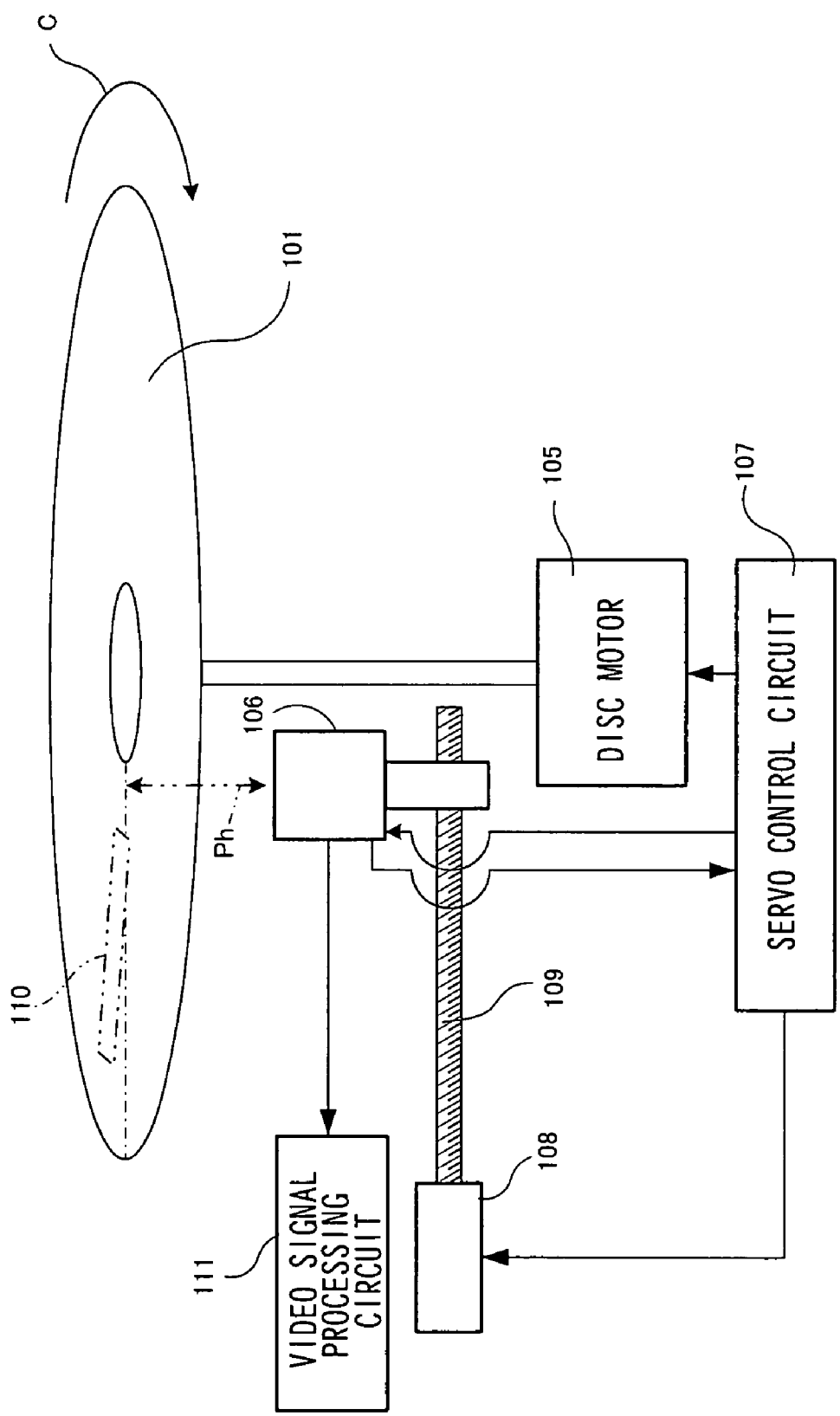
FIG. 6 is a structural diagram showing an analysis device in a conventional optical disc drive.
Figure 7:
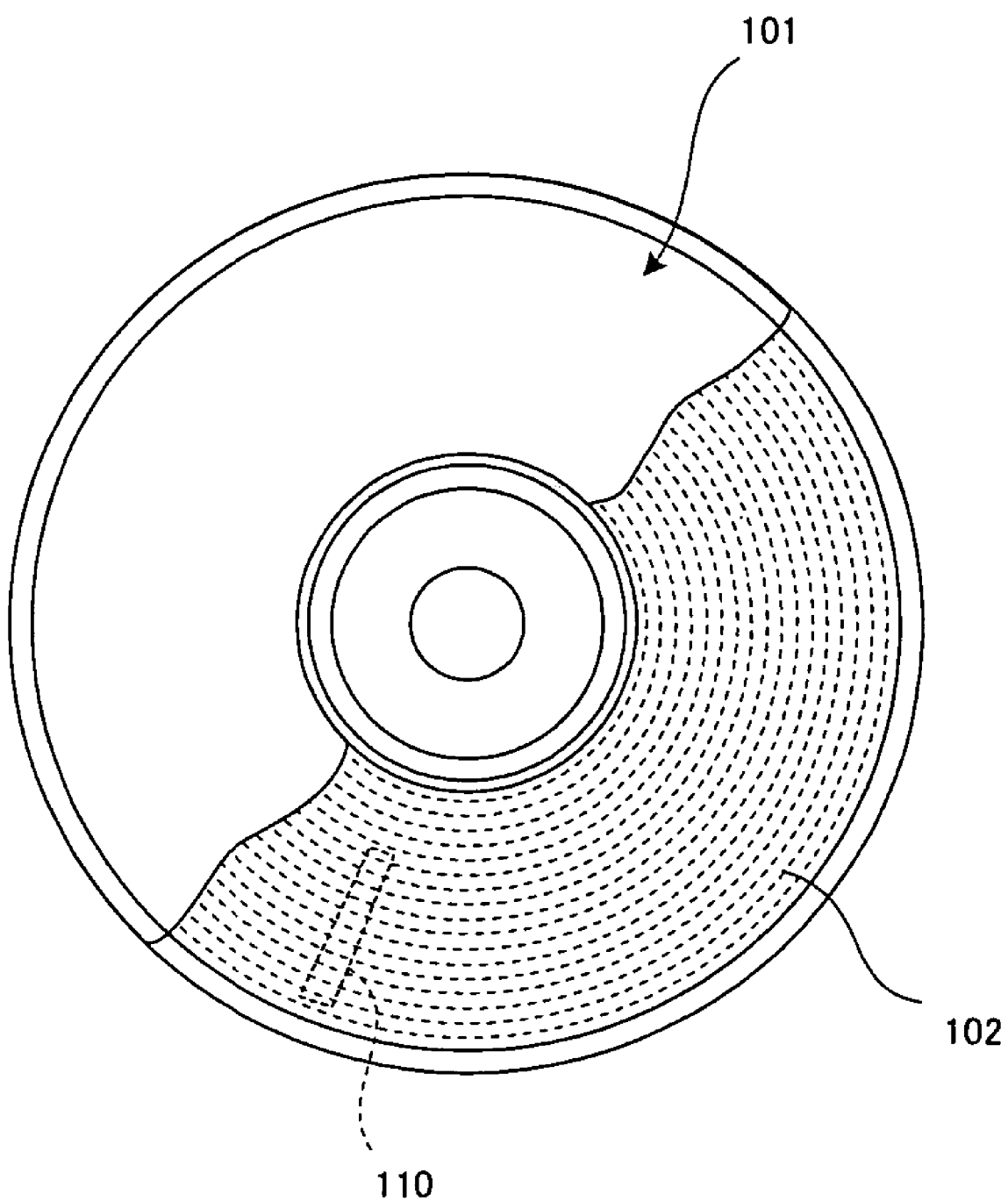
FIG. 7 is a partially cutaway plan view showing an optical disc according to the conventional art.
Figure 8:
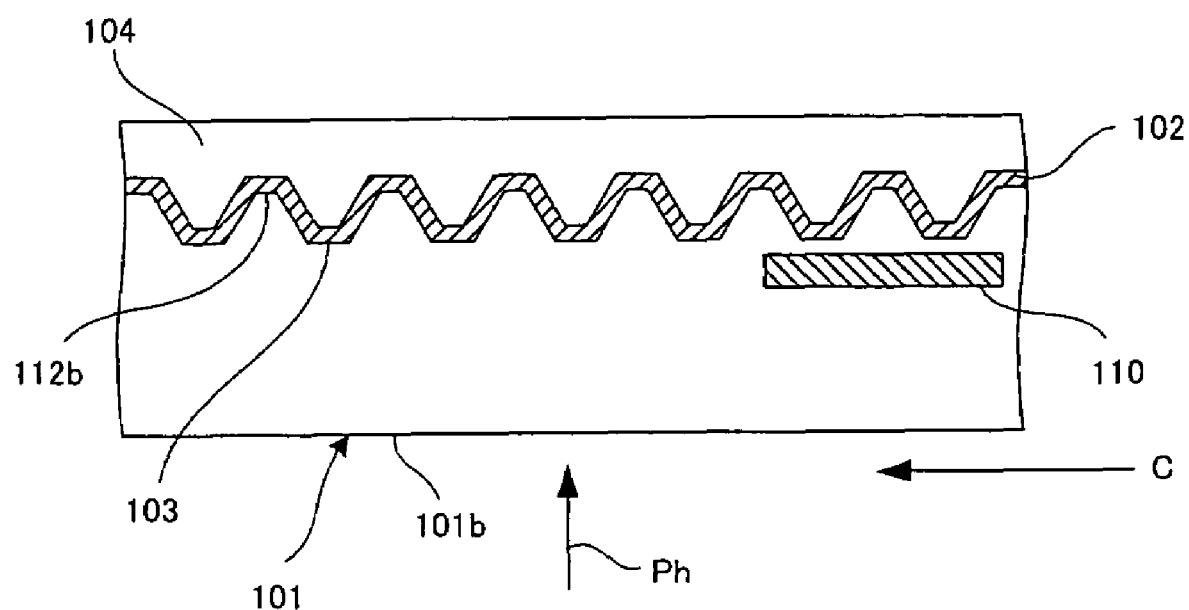
FIG. 8 is a sectional view taken along the tracking direction of the analysis disc.

The same constituent elements as FIGS. 6 to 8 showing the conventional art are indicated by the same reference numerals in the following explanation.

(EMBODIMENT 1)

FIGS. 1 to 4 show (Embodiment 1) of the present invention.

(Embodiment 1) is different from the conventional art in the structure of an analysis disc and the structure of an analysis device.

Figure 3:
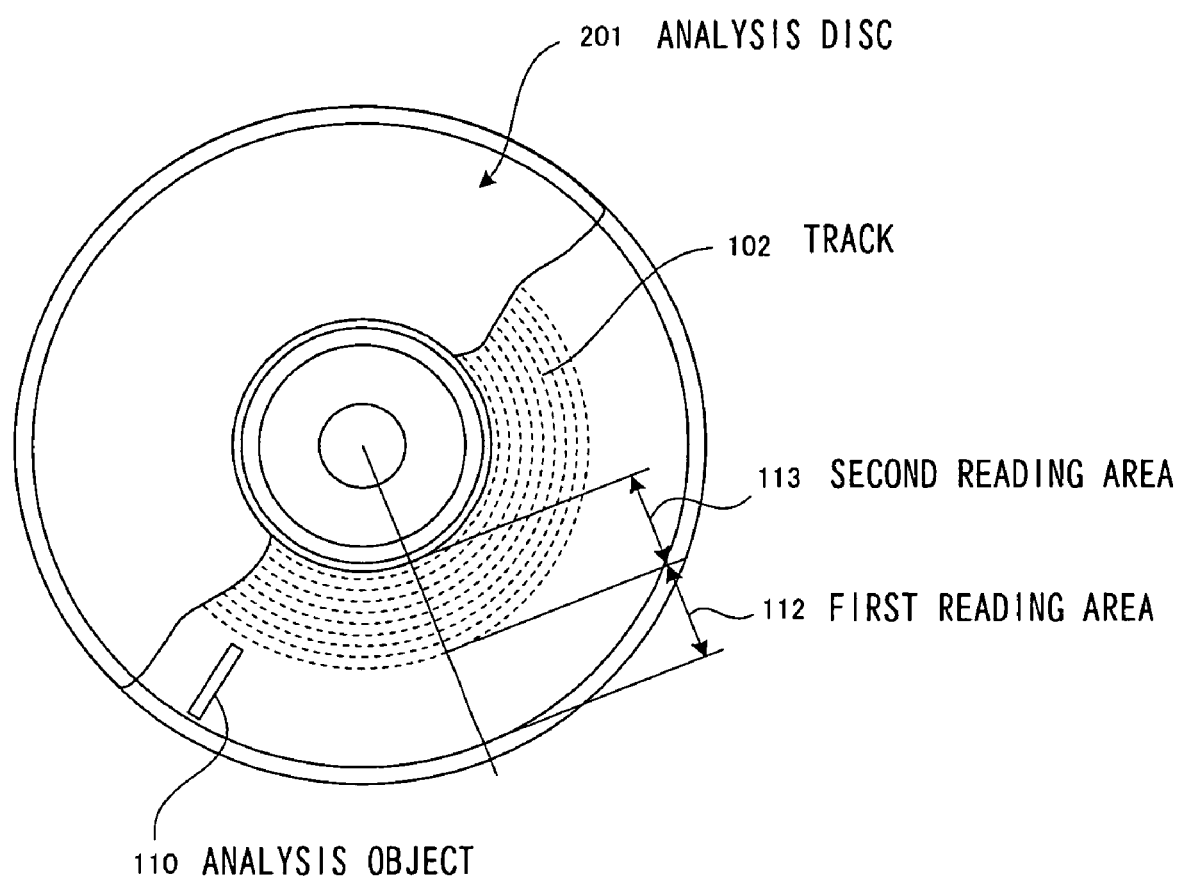
FIG. 3 is a partially cutaway plan view showing an analysis disc of the embodiment.
Figure 4:
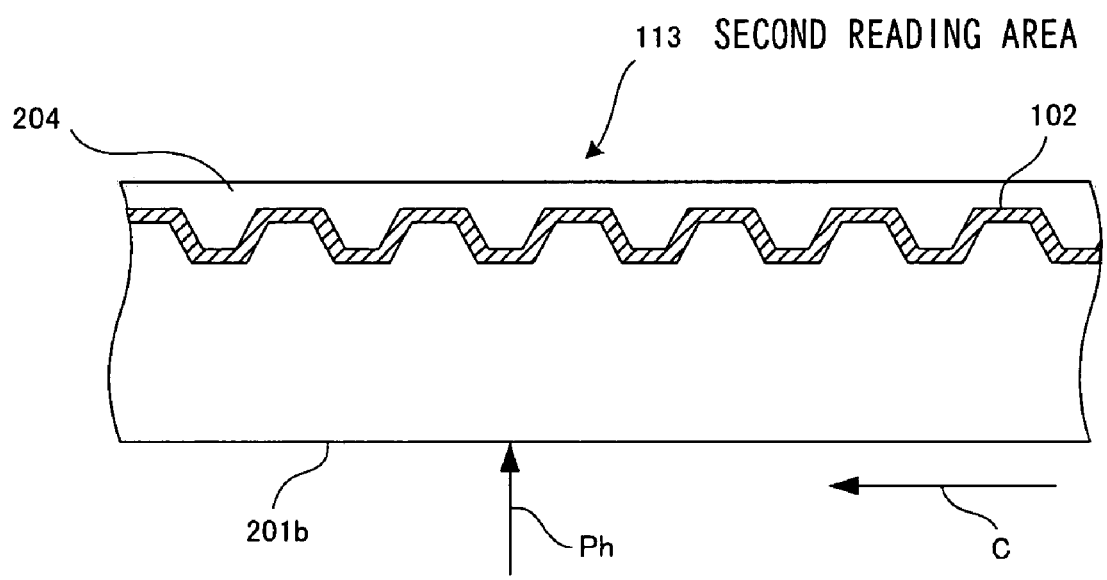
FIG. 4 is a sectional view taken along the tracking direction of a second reading area and a sectional view taken along the tracking direction of a first reading area of the analysis disc according to the embodiment.
Figure 4:
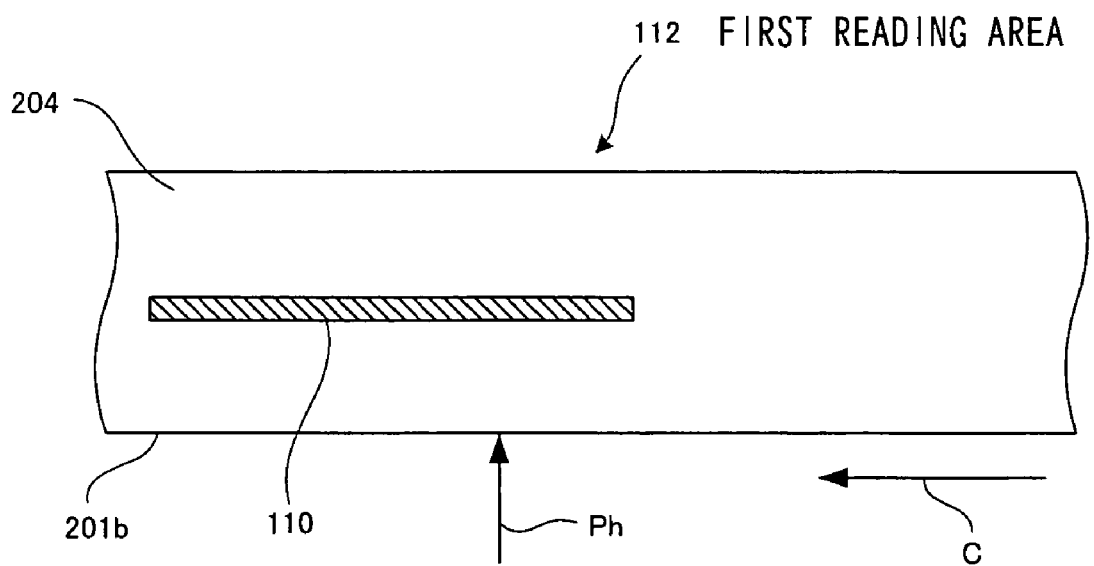

As shown in FIGS. 3 and 4, a first reading area 112 and a second reading area 113 are formed with different diameters on an analysis disc 201. When the first reading area 112 has a width W1 in the radial direction and the second reading area 113 has a width W2 in the radial direction, $W2 \geq W1$ is established.

As shown in FIG. 4(b), the first reading area 112 has an analysis object 110 disposed between a base 201b and a protective film 204. Tracks 102 formed in the second reading area 113 of FIG. 4(a) are not formed in the first reading area 112. The analysis object 110 is not disposed in the second reading area 113. In the analysis disc 201, the tracks 102b of an aluminum reflective layer are formed on a surface of the base 201b and information is recorded on pits and grooves 103 which are asperities finely formed on the tracks 102.

Figure 1:
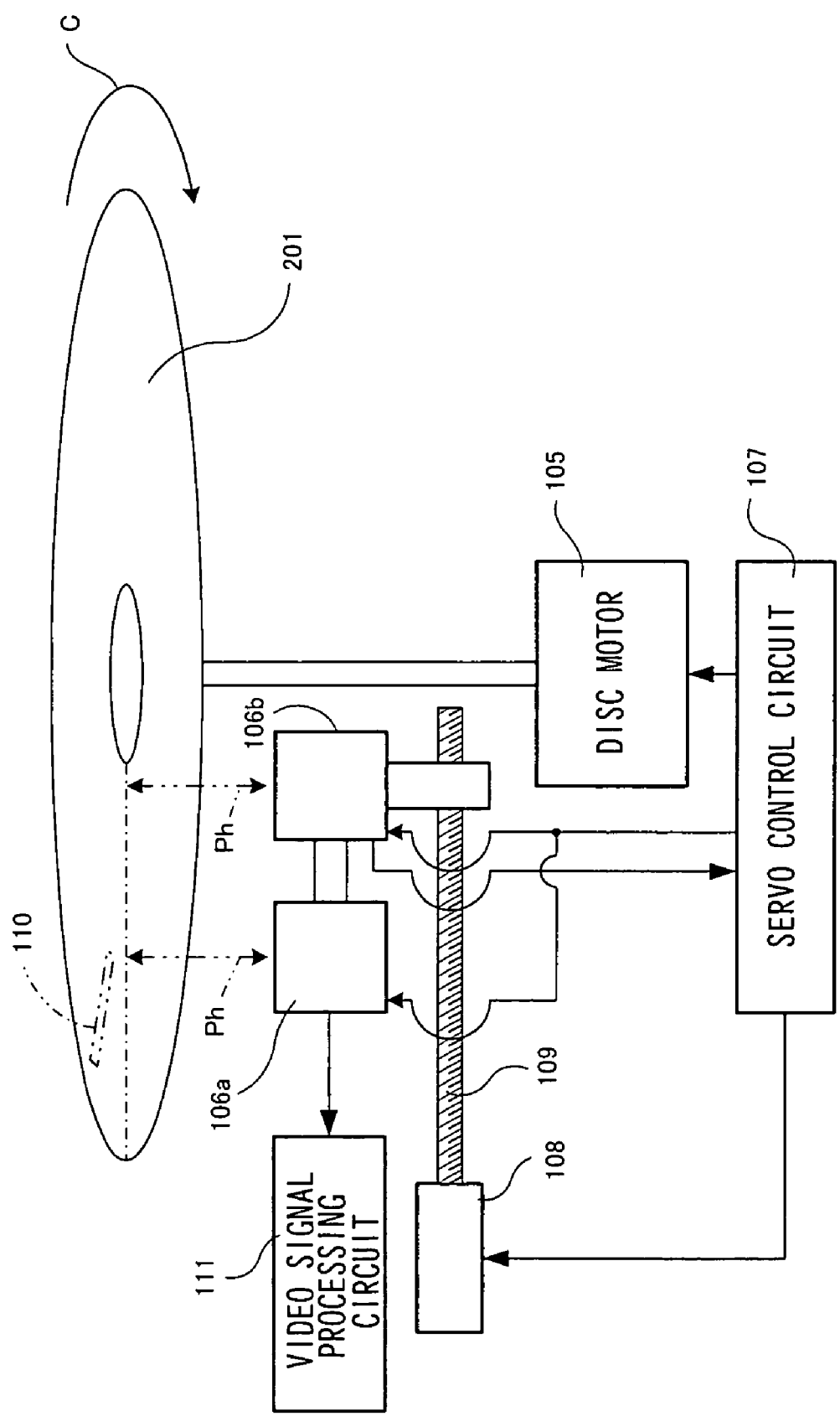
FIG. 1 is a structural diagram showing an analysis device according to (Embodiment 1) of the present invention.
Figure 2:
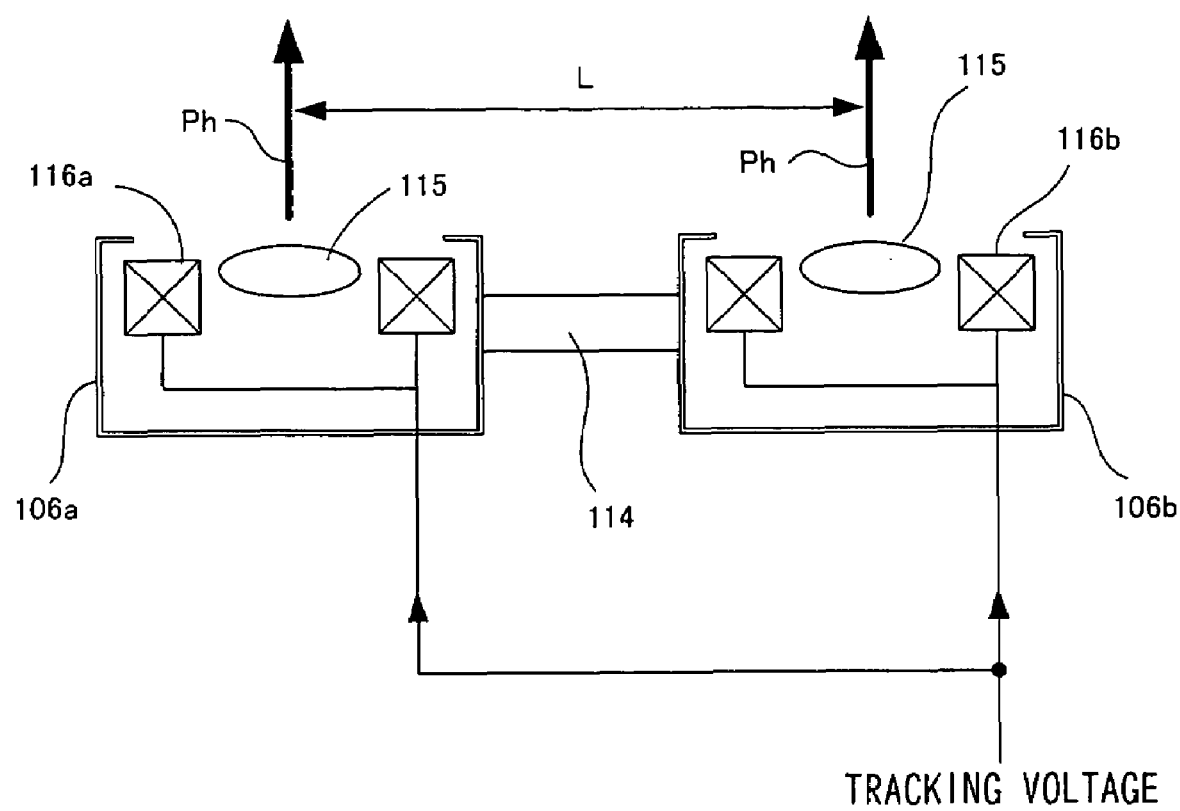
FIG. 2 is a structural diagram showing pickups of the embodiment.

As shown in FIGS. 1 and 2, first and second pickups 106a and 106b are provided in the analysis device where the analysis disc 201 is set.

The first pickup 106a irradiates the first reading area 112 of the set analysis disc 201 with a laser beam Ph and detects detection light from the first reading area 112. The second pickup 106b irradiates the second reading area 113 of the set analysis disc 201 with the laser beam Ph and detects track information from the second reading area 113.

In order to integrally move the first and second pickups 106a and 106b in the radial direction while keeping a constant interval L in the radial direction of the analysis disc 201 between the laser beam Ph emitted from the first pickup 106a and the laser beam Ph emitted from the second pickup 106b, for example, the first pickup 106a and the second pickup 106b are arranged along the length direction of a feed screw 109 (the same as the radial direction of the analysis disc 201) driven by a traverse motor 108, the pickups are connected to each other via a block 114, and only the second pickup 106b is screwed onto the feed screw 109.

Each of the first and second pickups 106a and 106b comprises a focus actuator (not shown) for driving a lens 115 in the focusing direction and tracking actuators 116a and 116b for driving the lens 115 in the lateral direction (radial direction) with respect to a surface of the analysis disc 201.

The length of the block 114 is set so as to irradiate the first reading area 112 with the laser beam Ph from the first pickup 106a and irradiate the second reading area 113 with the laser beam Ph from the second pickup 106b.

Further, the first and second pickups 106a and 106b separately perform focus control and the second pickup 106b traces the track 102. Moreover, the servo control circuit 107 is configured so as to apply, to a tracking actuator 116a of the first pickup 106a, the same signal as that of tracking voltage applied to a tracking actuator 116b of the second pickup 106b.

In this way, the servo control circuit 107 drives the traverse motor 108 and the tracking actuator 116b in such a way that the second pickup 106b traces the tracks 102 of the second reading area 113 while performing focus control. Hence, in the first reading area 112, the reading position of the first pickup 106a, which moves in the radial direction of the analysis disc 201 in an integrated manner with the second pickup 106b, also moves in the radial direction of the analysis disc 201.

Since the second reading area 113 does not have the analysis object 110, the second pickup 106b can correctly trace the tracks 102 by driving the traverse motor 108 and the tracking actuator 116b. Further, the servo control circuit 107 can perform stable CLV control on the disc motor 105 with a constant linear velocity based on accurate address information collected by the second pickup 106b which traces the tracks. The first pickup 106a can read an image of the analysis object 110 from the analysis disc 201 under stable CLV control while the position of the pickup 106a in the radial direction of the analysis disc 201 is accurately controlled by the tracking voltage of the second pickup 106b.

In the present embodiment, the single first pickup 106a reads the analysis object 110. As long as a movement is made in parallel with the second pickup 106b, a plurality of pickups may be provided for reading the first reading area 112. As the number of pickups increases, images can be obtained with higher efficiency.

Both of the first and second pickups 106a and 106b may have the function of reading an image of the analysis object from the analysis disc 201 and the function of reading track information. The first pickup 106a may have the function of reading an image of the analysis object from the analysis disc without the function of reading the track information.

The above explanation described that the second reading area 113 is provided on the inner edge of the analysis disc and the first reading area 112 is provided on the outer edge of the analysis disc. The first reading area 112 may be provided on the inner edge of the analysis disc and the second reading area 113 may be provided on the outer edge. In (Embodiment 1), it is necessary to set whether the second reading area 113 should be disposed on the inner edge or the outer edge of the analysis disc 201 and to specify from which of the two pickups the servo control circuit 107 should receive input information for calculating a tracking voltage.

(EMBODIMENT 2)

In (Embodiment 1), it is necessary to set whether the second reading area 113 should be disposed on the inner edge or the outer edge of the analysis disc 201. Automatic processing can be performed by adding a unit to decide from which of two pickups address information and so on are obtained, the address information being obtained by tracing tracks, and a servo control circuit 107 or the like is configured so as to perform automatic switching to cause a pickup having detected the address information and so on to act as a second pickup 106b and the other pickup to act as a first pickup 106a.

In the case of (Embodiment 2), as shown in FIG. 3, the first reading area 112 does not have tracks 102. In the case of (Embodiment 1), the same operations are expected also by an analysis disc in which both of the first and second reading areas 112 and 113 have the tracks 102 and only the second reading area 113 does not have the analysis object 110.

(EMBODIMENT 3)

In the foregoing embodiments, the pickup is divided as the first pickup 106a and the second pickup 106b, thereby obtaining an image of the analysis object 110 in a three-dimensional manner.

That is, the focus position of the second pickup 106b is automatically controlled on a pit and groove of the track 102, whereas an image of the analysis object 110 is obtained in a three-dimensional manner based on a difference obtained by changing the focus position of the first pickup 106a to the upper part or the lower part of the analysis object 110 and repeating tracing.

Figure 5:
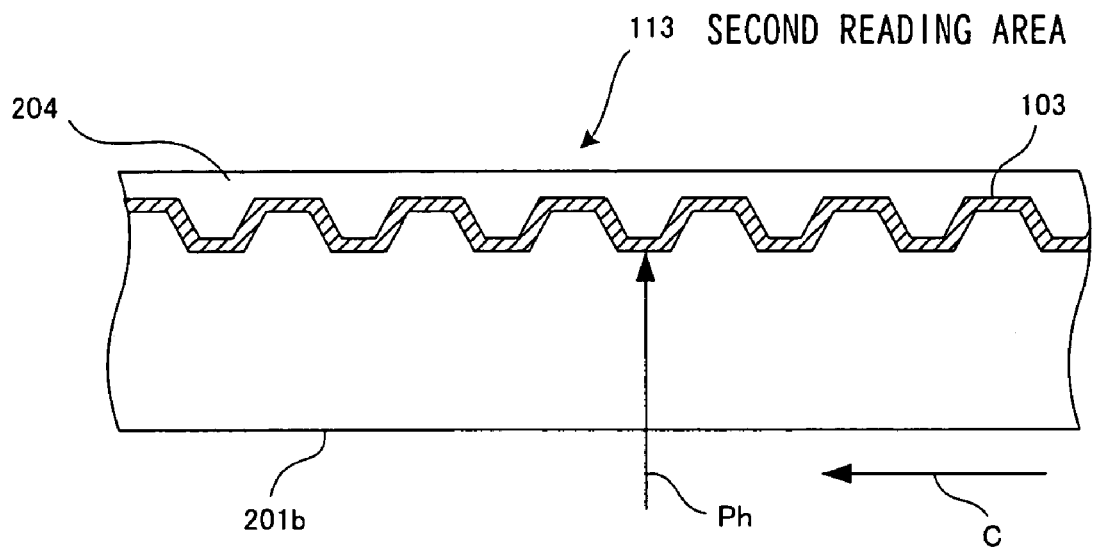
FIG. 5 is a diagram showing a concrete example of focus control in an analysis device according to (Embodiment 3) of the present invention.
Figure 5:
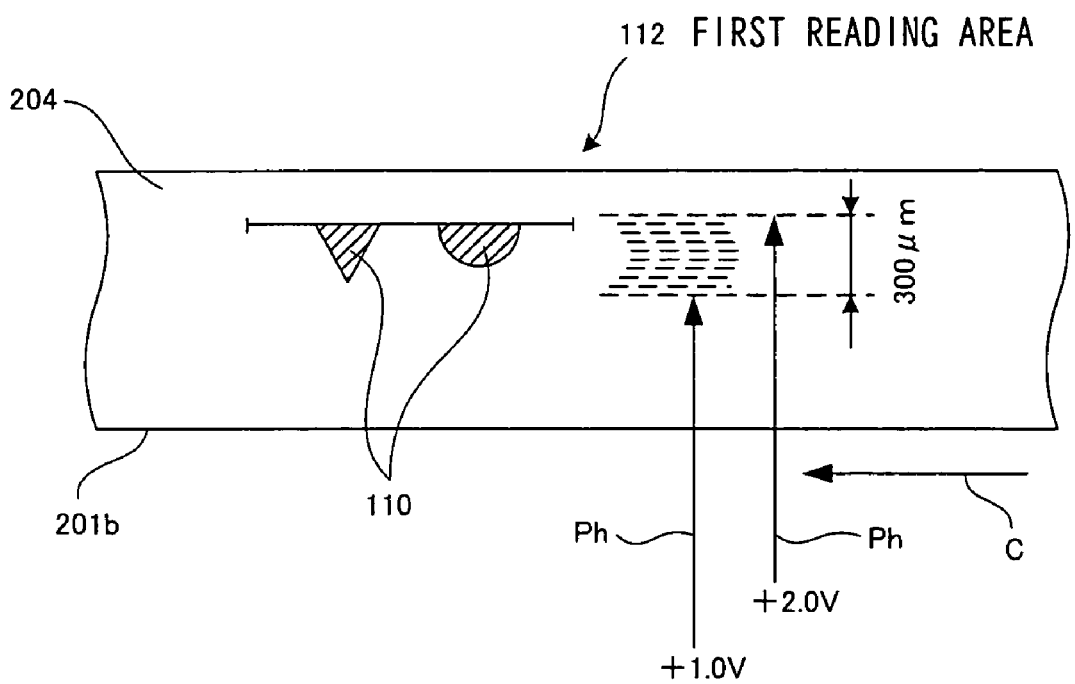

(Embodiment 3) shown in FIG. 5 will be more specifically described below.

In order to obtain a signal of the track, the focus position of a second pickup 106b has to be set on a pit and groove 103 on the mirror surface of an optical disc as shown in FIG. 5(a).

In contrast to the second pickup 106b, the focus position of a first pickup 106a can be set at a given focus position to perform tracing because track information does not have to be obtained.

By using this characteristic, the just focused position of the first pickup 106a is deliberately offset in stages to repeatedly obtain data. Thus, the video data of an analysis object 110 is obtained in a three-dimensional manner.

To be specific, regarding the focus position of the first pickup 106a, the focus actuator of the first pickup 106a is fed with a voltage which is obtained by offsetting in stages a focus voltage applied to the focus actuator of the second pickup 106b.

For example, it is assumed that a focus voltage of +1.5 V is necessary for enabling the second pickup 106b to focus on the tracks of the disc and a focus travel distance/focus applied voltage is 300 μm/V, which is the characteristic of the pickup.

In this case, +1 V is applied to the focus actuator of the first pickup 106a and tracing is first performed to obtain data, and then, +1.1 V is applied to obtain data in the subsequent tracing on the same part. In this way, a voltage applied to the focus coil of the first pickup 106a is successively increased by 0.1 V to increase a focus voltage to +2.0 V, and then, data is obtained. Thus, in this case, the 300-μm thickness of the analysis object 110 of the optical disc is traced with ten-split resolution. FIG. 5(b) shows an example where the analysis object 110 of the first reading area 112 is shown in a three dimensional manner. Dotted lines indicate just focused positions where a focus voltage applied to the focus actuator of the first pickup 106a is changed.

In this way, an image can be also obtained for a difference in shape along the thickness direction of the analysis object 110.

As described above, according to the present invention, even when an analysis disc is an optical disc having an analysis object therein, it is possible to accurately perform tracking control on pickups without being affected by the analysis object, stably control the rotation of the analysis disc without being affected by the analysis object, and extract a clear image of the analysis object.

The invention claimed is:

1. An analysis device for irradiating with detection light an analysis disc having an analysis object therein, and for reading a state of such an analysis object, wherein the analysis device configured for receiving an analysis disc in which a first reading area having an analysis object therein and a second reading area not having an analysis object therein are recorded, respectively, in different diameter ranges, the analysis device, comprising:

a first pickup for irradiating the first reading area of an analysis disc with detection light and detecting detection light from the first reading area, and a second pickup for irradiating the second reading area of an analysis disc with detection light and detecting track information from detection light of the second reading area, wherein means for controlling the device to keep a constant interval in a radial direction of the analysis disc between the first pickup and the second pickup, and to move the first and second pickups in the radial direction, and means for supplying a tracking signal to a tracking actuator of the second pickup so as to drive an optical path of the second pickup in the radial direction of an analysis disc and trace a track, and a signal identical to the tracking signal of the second pickup is applied to a tracking actuator of the first pickup for driving an optical path of the first pickup in the radial direction of an analysis disc, so that an analysis object is read.

2. The analysis device according to claim 1, wherein the first pickup is capable of reading an image on a reading position of an analysis disc but not capable of reading track information.

3. The analysis device according to claim 1, wherein both of the two pickups are capable of reading an image on a reading position of an analysis disc and of reading the track information, and of automatic switching by causing one of the pickups which reads track information from an analysis disc to act as the second pickup and the other pickup to act as the first pickup.

4. The analysis device according to claim 1, wherein a plurality of first pickups are provided for reading the first reading area.

5. An analysis disc, in which a first reading area and a second reading area are formed with different disc radial widths, wherein an optically readable coded signal traceable by a pickup is recorded in the first and second reading areas, and an analysis object is present only in the first reading area.

6. The analysis device according to claim 1, wherein a focus voltage for causing the second pickup to focus on a track is a reference voltage, the second pickup is for detecting detection light from the second reading area not having an analysis object therein, so that a voltage, obtained by adding an offset voltage, to an reference voltage is applied to a focus actuator of the first pickup for detecting detection light from the first reading area having an analysis object therein, thereby to trace analysis object to obtain an image, and the offset voltage is variable to change a focus position of the first pickup, thereby to repeatedly trace an analysis object to obtain an image of an analysis object in a three-dimensional manner.

* * * * *